(12) United States Patent
Vyverberg et al.

(10) Patent No.: US 6,455,722 B1
(45) Date of Patent: Sep. 24, 2002

(54) PROCESS FOR THE PRODUCTION OF PENTAERYTHRITOL PHOSPHATE ALCOHOL

(75) Inventors: Frederick J. Vyverberg, Lafayette; Robert W. Chapman, Mount Vernon, both of IN (US)

(73) Assignee: Pabu Services, Inc., Wilmington, DE (US)

( * ) Notice: Subject to any disclaimer, the term of this patent is extended or adjusted under 35 U.S.C. 154(b) by 0 days.

(21) Appl. No.: 09/896,710

(22) Filed: Jun. 29, 2001

(51) Int. Cl.⁷ ............................................. C07F 9/6571
(52) U.S. Cl. ..................................................... 558/74
(58) Field of Search ...................... 558/73, 74

(56) References Cited

U.S. PATENT DOCUMENTS

| | | | | |
|---|---|---|---|---|
| 3,342,903 A | * | 9/1967 | Grabhofer | 260/927 |
| 4,454,064 A | | 6/1984 | Halpern et al. | 260/974 |
| 5,237,085 A | | 8/1993 | Telschow et al. | 558/74 |
| 5,486,640 A | * | 1/1996 | Telschow et al. | 558/74 |
| 5,536,862 A | * | 7/1996 | Telschow et al. | 558/74 |

FOREIGN PATENT DOCUMENTS

CN    1281861    1/2001

* cited by examiner

*Primary Examiner*—Joseph K. McKane
*Assistant Examiner*—Golam M. M. Shameem
(74) *Attorney, Agent, or Firm*—Michael W. Ferrell

(57) ABSTRACT

A process for the production of pentaerythritol phosphate alcohol (PEPA) comprising reacting in the liquid phase phosphorus oxychloride ($POCl_3$) with pentaerythritol (PE) at a reaction temperature of at least about 100° C. in the presence of a solvent which is an alkane substituted with at least one halogen atom and having an atmospheric boiling point of about 40 to about 150° C., e.g., 1,2-dichloroethane (ethylene dichloride). The reaction pressure is sufficiently high to maintain the solvent in the liquid phase.

28 Claims, No Drawings

PROCESS FOR THE PRODUCTION OF PENTAERYTHRITOL PHOSPHATE ALCOHOL

BACKGROUND OF THE INVENTION

1. Field of the Invention

This invention relates to an improved process for the production of pentaerythritol phosphate alcohol.

2. Description of the Related Art

Pentaerytritol phosphate alcohol (PEPA) is a known effective flame retardant for plastics and other combustibles when used alone as an additive, or as part of a combination of additives. PEPA malt be synthesized by the liquid phase reaction of pentaerythritol and phosphorus oxychloride using a solvent to enable the reaction to go forward but in which the PEPA product has little if any solubility after the reaction solution is cooled. However, various problems with this process have been caused by certain undesirable properties of the solvents employed, e.g., excessive flammability in the case of ethers such as dioxane which also has a tendency to form explosive peroxides in contact with air and cannot be easily separated from by product HCl and water making solvent recycle difficult, or problems of purification and recycling due to the high boiling points and viscosities of solvents such as aryl phosphates. Thus, the use of a solvent which avoids some or all of the foregoing problems is very desirable.

U.S. Pat. No. 4,454,064, issued Jun. 12, 1984 to Halpern et al., discloses the preparation of PEPA by reacting approximately equimolar amounts of pentaerythritol (PE) and phosphorus oxychloride in a solvent at a temperature of about 75° C. to about 125° C., cooling the mixture to precipitate the PEPA, and isolating the PEPA. The disclosed solvents are dioxane, ethylene glycol dimethyl ether, diethylene glycol dimethyl ether, chlorobenzene, toluene, xylene, acetonitrile, sulfolane, and tetrachlorethylene.

U.S. Pat. No. 5,237,085, issued Aug. 17, 1993 to Telschow et al., teaches a process for the formation of pentaerythritol-based phosphorus heterocycles, e.g., PEPA, comprising the reaction of a pentaerythritol polyol with either a trivalent or pentavalent phosphorus compound, e.g., phosphorus oxychloride, using an arylphosphate solvent, at elevated temperature.

BRIEF SUMMARY OF THE INVENTION

In accordance with this invention, a process is provided for the production of pentaerythritol phosphate alcohol (PEPA) comprising reacting in the liquid phase phosphorus oxychloride ($POCl_3$) with pentaerythritol (PE), at a reaction temperature of at least about 100° C., and in the presence of a solvent which is an alkane, preferably methane, ethane or propane, substituted with at least one halogen atom and having an atmospheric boiling point of about 40 to about 150° C., the reaction pressure being sufficiently high to keep the solvent in the liquid phase. If the atmospheric boiling point of the solvent is lower than the desired temperature of reaction, then superatmospheric pressure is applied to keep the reaction in the liquid phase.

The foregoing solvents utilized in the process of this invention present fewer problems associated with the properties of the solvent as identified previously than many of the solvents for the reaction which are known in the art.

DETAILED DESCRIPTION OF THE INVENTION

Pentaerythritol phosphate alcohol (PEPA) is a white solid compound having a melting point of 213–218° C. and the following structural formula:

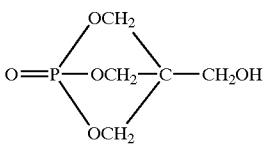

The CAS registry name of this compound is 2,6,7-trioxa-1-phosphabicyclo-[2,2,2]octane-4-methanol-1-oxide.

The PEPA is synthesized by reacting approximately equimolar amounts of phosphorous oxychloride and pentaerythritol (PE) in the liquid phase, and in the presence of any of a specific class of solvents for the reactants as defined hereinafter. The reaction proceeds in accordance with the following equation:

No catalyst is required for this reaction.

In general, when the amount of $POCl_3$ utilized in the reaction is 1 mole or slightly more per mole of PE, the mass yield of PEPA produced is relatively high, e.g., at least about 95% based on the $POCl_3$. Of course, the use of less than 1 mole of $POCl_3$ per mole of PE will reduce the overall yield of PEPA since the $POCl_3$ is the limiting reactant. As used herein, "mass yield" is defined as the amount of product recovered as a fraction of the theoretical amount of PEPA expected based on the quantity of limiting reactant charged to the vessel. However, it has been found that the employment of substantially more than 1 mole of $POCl_3$ per mole of PE tends to reduce the mass yield of PEPA based on the PE even though the PE in this case is the limiting reactant; see comparative Example B hereinafter. The apparent cause of this reduction in the mass yield of PEPA when $POCl_3$ is present in a relatively large excess is the occurrence of another reaction between $POCl_3$ and PE in accordance with the following equation:

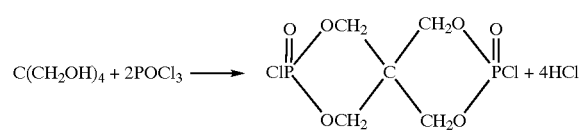

The phosphorus containing product of the reaction indicated in the latter equation is 3,9-dichloro-2,4,8,10-tetraoxa-3,9-diphosphaspiro[5,5]undecane-3,9-dioxide.

Taking into account the foregoing description of the reactions involved, the process of the invention is preferably carried out by employing no more than about 1.20 moles of $POCl_3$, more preferably no more than about 1.15 moles of $POCl_3$ and most preferably from about 0.95 to about 1.10 moles of $POCl_3$, per mole of PE.

As stated in the Brief Summary of the Invention, the solvent employed in the process is an alkane, preferably methane, ethane, or propane, substituted with at least one halogen atom, preferably chlorine, and having an atmospheric boiling point (b.p.) of at least about 40° C. and no higher than about 150° C. Preferably the atmospheric boiling point (b.p.) is in the range of about 80 to about 120° C. Some suitable solvents are:

1,2-dichloroethane (ethylene dichloride or EDC, b.p.=83.5° C.),
1,1-dichloroethane (ethylidene chloride, b.p.=57.3° C.),
1,1,1-trichloroethane (methyl chloroform, b.p.=74.1° C.), 1,1,2-trichloroethane (b.p.=113.8° C.),
1,1,1,2-tetrachloroethane (b.p.=130.5° C.),
trichloromethane (chloroform, b.p.=61.7° C.),
tetrachloromethane (carbon tetrachloride, b.p.=76.5° C.),
1,1-dichloropropane (b.p.=88.1° C.),
1,2-dichloropropane (b.p=–96.4° C.),
1,3-dichloropropane (b.p.=120.4° C.),
1,2,2-trichloropropane (b.p.=123–5° C.),
1,1-dibromoethane (ethylidene bromide, b.p.=108° C.),
1,2-dibromoethane (ethylene dibromide, b.p.=131.3° C.),
dibromomethane (methylene bromide, b.p.=97° C.),
1-bromopropane (n-propylbromide, b.p.=71° C.),
2-bromopropane (isopropylbromide, b.p.=59.4° C.),
1,1-dibromopropane (b.p.=133.5° C.),
iodoethane (ethyl iodide, b.p.=72.3° C.),
1-iodopropane (n-propyliodide, b.p.=102.4° C.),
2-iodopropane (isopropyl iodide, b.p.=89.4° C.),
1-bromo-3-chloropropane (b.p.=144° C.),
bromochloromethane (b.p.=68° C.), and
1-bromo-2-chloroethane (b.p.=106° C.)

The reaction is carried out at a temperature of at least about 100° C., preferably in the range of about 100 to about 150° C., and more preferably in the range of about 110 to about 130° C. If the solvent has an atmospheric boiling point below the desired reaction temperature, then superatmospheric pressure is applied to keep most of the solvent in the liquid phase. Consistent with this condition, the reaction pressure is in most cases in the range of 0 to about 70 psig, preferably in the range of about 20 to about 50 psig.

The process is carried out by reacting the PE with the $POCl_3$ in the presence of the solvent at the reaction temperature under superatmospheric pressure if necessary until close to the theoretical amount of HCl off-gas is evolved indicating substantial completion of the reaction. Such reaction time may be, for example, in the range of about 0.5 to about 8 hours and often in the range of about 1 to about 3 hours. The reaction may be carried out in batch, semi-continuous or continuous fashion. Due to the handling problems in feeding solid PE to the reactor (which could potentially be operating under pressure), batch reactions are preferred.

In a preferable embodiment of the process of the invention, PE is added to the solvent and the resulting slurry is heated to a reaction temperature at or close to the desired value with stirring. During such heating, if the atmospheric boiling point of the solvent is exceeded, the pressure in the reactor is allowed to increase by the evolution of HCl off-gas and a pressure control valve is preferably used to maintain the reactor pressure at a level which is sufficient to keep the solvent in the liquid phase. Phosphorus oxychloride ($POCl_3$) is then added portionwise, e.g., within a period of at least 5 minutes to about two hours while maintaining the reaction temperature at the desired level. The pressure control valve allows the HCl by-product to escape to a scrubber while keeping the reaction pressure constant. The substantial completion of HCl evolution indicates the end of the reaction period and the reactor is cooled to a lower temperature at which most of the PEPA product is separated out and the resulting slurry is suitable for filtration. Such lower temperature is below the boiling point of the solvent if such boiling point was below the reaction temperature and a superatmospheric reaction pressure was employed. Room temperature is often suitable as the temperature to which the reaction slurry is cooled although such cooling may be to a temperature somewhat higher than room temperature. The cooled slurry is then filtered, and the PEPA product washed, if necessary, with appropriate washing liquids and dried by well-known methods.

Using the process of this invention, a PEPA product can be obtained with relatively low reaction time, at a mass yield of at least about 95% of the theoretical yield based on the reactant present in limiting amount, allowing for high productivity, and with a PEPA purity of at least about 80%. The product can be used directly or, if desired, can be further purified by known methods.

The following examples further illustrate the invention.

EXAMPLE 1

A glass stirred pressure reactor was charged with 87.5 g (0.64 mole) of pentaerythritol (PE) and 500 ml. of 1,2-dichloroethane (EDC) to form a slurry. The reactor was fitted with a pressure valve set to release gas at 30 psig into a water scrubber. The resulting stirred slurry was heated to 115° C. and 103.5 g (0.67 mole) of $POCl_3$ were added over a period of five minutes. Off gassing began within 30 minutes and continued for 2.5 hours until 70 g of HCl were collected. The total reaction time was about 3 hours. The reaction mass was cooled to room temperature, the pressure released and the reaction slurry filtered. The separated product was dried at 85° C. to yield 113.3 grams of white solids (98% mass yield) containing 84% PEPA by liquid chromatography (LC).

These results show that an almost ideal mass yield of high quality product can be obtained from the process of the invention with the short reaction time resulting in high productivity.

COMPARATIVE EXAMPLE A

This example illustrates the effect of operating the process at a reaction temperature below the prescribed minimum of 100° C.

A glass stirred reactor connected through a water cooled condenser to an acid scrubber was charged with 75 g (0.55 mole) of PE and 262.5 g of EDC. The reactor was heated to 80° C. and 87.8 g (0.57 mole) of $POCl_3$ were added over 105 minutes. Slow off-gassing began around 70 minutes after the start of the addition of $POCl_3$ and continued for another 7 hours until 55.4 g of HCl were collected. The total reaction time was about 9 hours. The heating was then stopped, the reaction mass cooled to room temperature and the resulting product slurry filtered. The separated product was dried at 105° C. to yield 94.0 g of white solids (95% mass yield) containing only 55% of PEPA by LC.

The foregoing results indicate that operating the process at a temperature substantially below the minimum of 100° C. results in relatively low conversion to PEPA even after a relatively long reaction time.

EXAMPLE 2

This example illustrates the effect of utilizing a comparatively large excess of $POCl_3$ relative to PE in carrying out the process.

A glass stirred pressure reactor was charged with 87.4 g (0.64 mole) of PE and 568 ml. of EDC. The reactor was fitted with a pressure valve set to release gas at 30 psig into a water scrubber. The resulting stirred slurry was heated to 115° C. and 122 g (0.80 mole) of $POCl_3$ were added over 30 minutes. Off-gassing of HCl began within 20 minutes and continued until 69 g were collected 2.5 hours later. The total reaction time was about 3.5 hours. The heating was then discontinued, the reaction mass cooled to room temperature, the pressure released and the slurry filtered. The separated product was dried at 105° C. to yield 103.5 g of white solids (89% mass yield) containing 86% PEPA by LC.

EXAMPLE 3

This example illustrates the effect of using comparatively higher temperature and pressure conditions in carrying out the inventive process.

A glass stirred pressure reactor was charged with 87.6 g (0.64 mole) of PE and 568 ml. of EDC. The reactor was fitted with a pressure valve set to release gas at 45 psig into a water scrubber. The resulting stirred slurry was heated to 130° C. and 122 g (0.80 mole) of $POCl_3$ were added over 28 minutes. Off-gassing of HCl began just before the addition was complete and continued until 70 g were collected 2 hours later. The total reaction time was about 2.5 hours. The heating was then discontinued, the reaction mass cooled to room temperature, the pressure released and the slurry filtered. The separated product was dried at 105° C. to yield 110.2 g of white solids (95% mass yield) containing 83% PEPA by liquid chromatography (LC).

What is claimed is:

1. A process for the production of pentaerythritol phosphate alcohol (PEPA) comprising reacting in the liquid phase phosphorus oxychloride ($POCl_3$) with pentaerythritol (PE) at a reaction temperature of at least about 100° C. in the presence of a solvent which is an alkane substituted with at least one halogen atom and having an atmospheric boiling point of about 40 to about 150° C., the reaction pressure being sufficiently high to maintain the solvent in the liquid phase, the reaction resulting in the production of PEPA and HCl by-product.

2. The process of claim 1 wherein said alkane is methane, ethane or propane.

3. The process of claim 2 wherein said halogen atom is chlorine.

4. The process of claim 3 wherein said solvent is 1,2-dichloroethane (ethylene dichloride or EDC).

5. The process of claim 1 wherein said atmospheric boiling point of the solvent is below said reaction temperature and said reaction pressure is superatmospheric.

6. The process of claim 1 wherein said reaction temperature is in the range of about 100 to about 150° C.

7. The process of claim 6 wherein said reaction temperature is in the range of about 110 to about 130 ° C.

8. The process of claim 1 wherein said reaction pressure is in the range of about 0 to about 70 psig.

9. The process of claim 8 wherein said reaction pressure is in the range of about 20 to about 50 psig.

10. The process of claim 1 wherein the atmospheric boiling point of said solvent is in the range of about 80 to about 120° C.

11. The process of claim 1 wherein said molar ratio of $POCl_3$ to PE is in the range of about 0.9 to about 1.10 moles of $POCl_3$ per mole of PE.

12. The process of claim 1 carried out by adding the total amount of PE to the solvent, heating the resulting slurry in the reaction zone to a temperature close to the desired reaction temperature while allowing the pressure in the reaction zone to increase if the atmospheric boiling point is below the reaction temperature, adding the $POCl_3$ portionwise to the reaction zone, maintaining the reaction temperature at the desired level, and continuing the reaction until the substantial completion of the evolution of HCl off-gas.

13. The process of claim 12 wherein the atmospheric boiling point of the solvent is below the reaction temperature and the pressure in the reaction zone is allowed to rise to a superatmospheric level by the accumulation of HCl off-gas.

14. The process of claim 1 wherein the reaction time is in the range of about 0.5 to about 8 hours.

15. The process of claim 14 where said range of reaction time is about 1 to about 3 hours.

16. The process of claim 12 wherein said $POCl_3$ is added within a time range of about 5 minutes to about 2 hours.

17. The process of claim 12 wherein PEPA is produced before further purification in a mass yield of at least 95% of the theoretical yield based on the reactant present in limiting amount and with a PEPA purity of at least about 80%.

18. A process for the production of pentaerythritol phosphate alcohol (PEPA) comprising reacting in the liquid phase phosphorus oxychloride ($POCl_3$) with pentaerythritol (PE) at a molar ratio of no more than about 1.20 mole of $POCl_3$ per mole of PE and at a reaction temperature of at least about 100° C. in the presence of a solvent which is an alkane substituted with at least one halogen atom and having an atmospheric boiling point of 40 to about 150° C., the reaction pressure being sufficiently high to maintain the solvent in the liquid phase, the reaction resulting in the production of PEPA and HCl by-product.

19. The process of claim 18 wherein said molar ratio is no more than about 1.15.

20. The process of claim 18 wherein said alkane is methane, ethane or propane.

21. The process of claim 20 wherein said halogen atom is chlorine.

22. The process of claim 21 wherein said solvent is 1,2-dichloroethane (ethylene dichloride or EDC).

23. The process of claim 18 wherein said atmospheric boiling point of the solvent is below said reaction temperature a,id said reaction pressure is superatmospheric.

24. The process of claim 18 wherein said reaction temperature is in the range of about 100 to about 150° C.

25. The process of claim 24 wherein said reaction temperature is in the range of about 110 to about 130° C.

26. The process of claim 1 wherein said reaction pressure is in the range of about 0 to about 70 psig.

27. The process of claim 26 wherein said reaction pressure is in the range of about 20 to about 50 psig.

28. The process of claim 1, wherein said solvent is selected from the group consisting of 1,2-dichloroethane (ethylene dichloride or EDC), 1,1-dichloroethane (ethylidene chloride), 1,1,1-trichloroethane (methyl chloroform), trichloromethane (chloroform) tetrachloromethane (carbon tetrachloride), 1,1-dichloropropane, 1-bromopropane (n-propylbromide), 2-bromopropane (isopropylbromide), iodoethane (ethyl iodide), 2-iodopropane (isopropyl iodide), and bromochloromethane.

* * * * *